United States Patent [19]

Vargas, Jose M. et al.

[11] Patent Number: 5,059,718

[45] Date of Patent: Oct. 22, 1991

[54] OXO PROCESS FOR INCREASING YIELD OF OXO ALCOHOL

[75] Inventors: Vargas, Jose M., Baton Rouge, La.; Jean A. Hanin, Rixensart, Belgium; John C. Reisch, Hilton Head, S.C.

[73] Assignee: Exxon Chemical Patents Inc., Linden, N.J.

[21] Appl. No.: 586,906

[22] Filed: Sep. 24, 1990

[51] Int. Cl.$^5$ .................... C07C 29/14; C07C 29/74
[52] U.S. Cl. .................... 568/881; 568/810; 568/880
[58] Field of Search ............... 568/462, 880, 881, 810

[56] References Cited

U.S. PATENT DOCUMENTS

| | | | |
|---|---|---|---|
| 3,925,490 | 12/1975 | Reich et al. | 568/881 |
| 3,935,285 | 1/1976 | Tummes et al. | 260/638 |
| 4,401,834 | 8/1983 | King | 568/881 |
| 4,404,119 | 9/1983 | Lagace et al. | 252/413 |
| 4,419,195 | 12/1983 | Young | 204/78 |
| 4,656,215 | 4/1987 | Hanin et al. | 524/376 |
| 4,658,068 | 4/1987 | Hanin | 568/451 |
| 4,683,343 | 7/1987 | Hanin et al. | 568/594 |

FOREIGN PATENT DOCUMENTS 756877  3/1971  Belgium .................... 568/881

OTHER PUBLICATIONS

Kirk-Othmer, Encyclopedia of Chemical Technology, vol. 16, 3rd Edition, John Wiley & Sons, pp. 637-653, 1981.

Primary Examiner—Werren B. Lone
Attorney, Agent, or Firm—J. J. Mahon

[57] ABSTRACT

Improved oxo process for preparing higher alcohols by hydrolyzing prior to hydrogenation a demetalled hydroformylation reaction product in the presence of an alumina catalyst having a surface area between 40 to about 60 m$^2$/g.

9 Claims, 1 Drawing Sheet

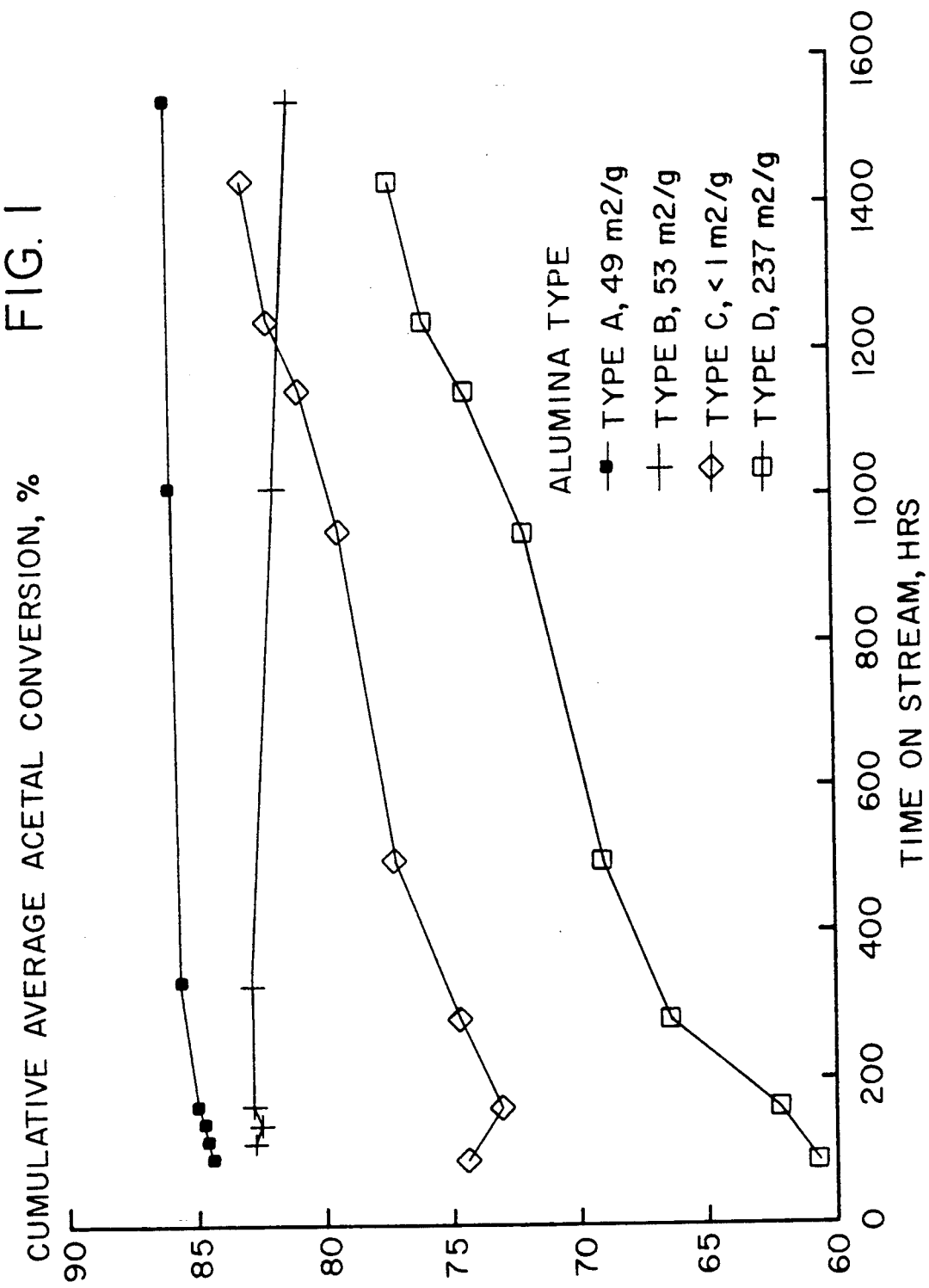

OXO PROCESS FOR INCREASING YIELD OF OXO ALCOHOL

BACKGROUND OF THE INVENTION

This invention relates to an improved process for preparing oxo alcohols, and more specifically to an improved process for preparing such alcohols at a higher yield by reducing the concentration of impurities which represent an irreversible yield loss.

The oxo process is the commercial application of the hydroformylation reaction for making higher alcohols from olefins. In the oxo process, an olefin reacts with carbon monoxide and hydrogen at elevated temperature and pressure in the presence of a transition metal catalyst, typically a cobalt or rhodium carbonyl complex, to produce a hydroformylation reaction product intermediate. This intermediate is predominantly two isomeric aldehydes as illustrated by the following chemical reaction:

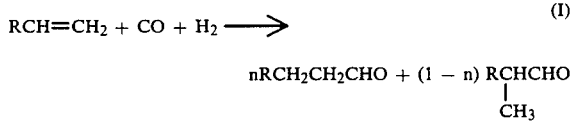

Following removal of the transition metal catalyst from the hydroformylation reaction product, the demetalled intermediate is converted by hydrogenation to alcohols.

The demetalled hydroformylation reaction product intermediate contains not only higher aldehydes, but also higher alcohols, unreacted olefin and secondary products. The secondary products include acetal and formate impurities. The acetal impurities will undergo chemical reaction during hydrogenation of the demetalled reaction product intermediate as illustrated by the following reaction:

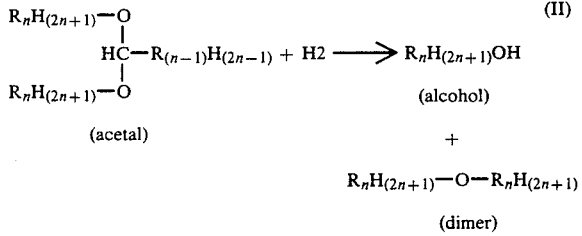

As illustrated by this reaction, the acetal impurities are converted to higher alcohol and undesired dimers. The dimers are not readily converted to the desired higher alcohol and thus represent an irreversible yield loss.

The formate impurities also undergo chemical reaction during hydrogenation of the demetalled intermediate as illustrated by the following reaction:

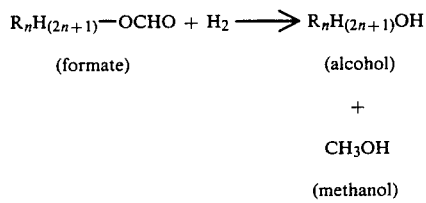

The formate impurities are converted to higher alcohol and methanol. Methanol is an undesired product because it is difficult to remove from product streams and it is difficult to treat in conventional anaerobic waste treatment plants.

Efforts have been made to reduce the adverse effects of acetal and formate impurities in the hydroformylation reaction product. U.S. Pat. Nos. 4,658,068; 4,656,215 and 4,683,343 each describe distilling the demetalled hydroformylation reaction product after hydrogenation to separate the desired alcohol from a higher boiling heavy oxo fraction, which would contain the acetal and formate impurities. This heavy oxo fraction is subsequently subjected to steam cracking in the presence of an active metal oxide or pseudo-metal oxide catalyst at elevated temperatures to form a cracked mixture containing an increased concentration of higher alcohol and aldehyde. The cracked mixture can then be recycled to the hydroformylation or hydrogenation steps of the process. Although this process significantly reduces the adverse consequences of the acetal and formate impurities in the hydrogenated reaction product, it would be desirable to utilize a process that reduces the concentration of these impurities before the hydrogenation step.

To that end, U.S. Pat. Nos. 4,401,834 (King patent) and 3,935,285 (Tummes patent) each disclose hydrolyzing the demetalled hydroformylation reaction product prior to hydrogenation in an attempt to convert a significant amount of the acetal and formate impurities to higher alcohol and aldehyde, as well as formic acid. Formic acid can be decomposed during hydrogenation to hydrogen and carbon dioxide. The hydrolysis reaction for the acetal and formate impurities and the subsequent decomposition of formic acid can be illustrated as follows:

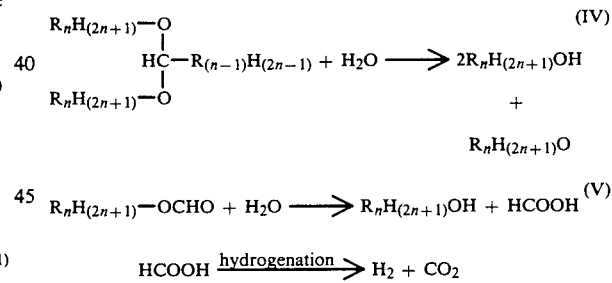

The King patent discloses hydrolyzing the demetalled hydroformylation reaction product in the absence of added acidic compounds at elevated temperatures and pressures. Although some conversion of the impurities to higher aldehydes and alcohols is achieved, the slight increase in conversion does not offset the time and expense required to carry out an additional hydrolysis step in the oxo process.

The Tummes patent discloses hydrolyzing the demetalled product in the presence of a high surface area alumina catalyst at elevated temperatures and essentially atmospheric pressure. Although slightly higher conversions may be achieved using the high surface area alumina catalyst relative to an uncatalyzed hydrolysis, the conversion is still inadequate. Additionally, the Tummes hydrolysis requires extremely high temperatures, which is uneconomical because of dramatically increased energy requirements, and a concentration of water or steam greater than the solubility limit of the water in the hydrocarbon phase. Therefore, an additional phase separation would be required to separate the water from the desired product.

In view of the deficiencies of the prior art, an improved oxo process is needed which would reduce the concentration of acetal and formate impurities in the demetalled hydroformylation reaction product prior to hydrogenation. More specifically, an improved process for increasing the concentration of oxo alcohols is needed which converts a substantial amount of acetal and formate impurities in the demetalled product to higher aldehyde and alcohol prior to hydrogenation.

SUMMARY OF THE INVENTION

The invention is an improvement in the process for increasing the yield of an oxo alcohol prepared from the hydrogenation of a demetalled hydroformylation reaction product by hydrolyzing prior to hydrogenation the reaction product at conditions sufficient to convert an amount of acetal impurities in the reaction product to the corresponding aldehyde or alcohol. In particular, the improvement comprises the step of conducting the hydrolysis in the presence of a catalytically effective amount of an alumina catalyst having a surface area between about 40 to about 60 m$^2$/g.

Surprisingly, conducting the hydrolysis in the presence of the low surface area alumina catalyst specified increases the conversion of acetal impurities in the demetalled hydroformylation reaction product to the corresponding aldehyde or alcohol, when compared with the conversion achieved by conducting the hydrolysis without the presence of a catalyst or the presence of a high surface area alumina catalyst. This translates into a direct increase in yield of oxo alcohol prepared following hydrogenation of the hydrolyzed reaction product.

The hydrolysis can be carried out under a wide range of operating conditions, including lower temperatures relative to the known art, and at a concentration of water or steam which does not exceed the solubility limit of the water or steam in the hydrocarbon phase. Additionally, catalyzing the hydrolysis in the presence of the low surface area alumina catalyst increases conversion of formate impurities in the demetalled reaction product to the alcohol and formic acid relative to the known art. This again translates into an increased oxo alcohol yield following hydrogenation and reduces treating methanol in an anaerobic waste treatment plant.

The improved process of this invention is useful for preparing oxo alcohols. These higher molecular weight alcohols are used in the manufacture of plasticizers, lubricating oil additives, detergents and defoamers.

DETAILED DESCRIPTION OF THE INVENTION

For purposes of describing this invention, hydroformylation reaction product is the reaction product of an olefin with carbon monoxide and hydrogen carried out by the oxo process. The oxo process is well known and described in detail in Kirk-Othmer, *Encyclopedia of Chemical Technology*, Volume 16, 3rd ed., John Wiley & Sons, pp. 637-653, 1981. The reaction product is typically a mixture of higher aldehyde and alcohol, unreacted feed and secondary products. These secondary products usually include high boiling compounds such as aldols, esters and ethers, as well as the acetal and formate impurities.

"Demetalled" hydroformylation reaction product is reaction product substantially depleted of the transition metal catalyst required for the hydroformylation reaction. Processes for demetalling the reaction product are described in the Kirk-Othmer encyclopedia, as well as U.S. Pat. Nos. 4,419,195 and 4,404,119.

The olefin feedstock for the hydroformylation reaction is typically a commercial olefin feedstock which may include linear and branched $C_{2-17}$ monoolefins. Preferably, the olefin feedstock contains a significant amount of a branched $C_{5-12}$ monoolefin. The preferred olefins include amylenes from petroleum cracking; heptenes, octenes, nonenes, and dodecenes from fractionation of oligomers of $C_{3-4}$ olefins; and octenes from dimerization and codimerization of isobutylene and 1- and 2-butenes.

The alumina catalyst employed in the hydrolysis step has a BET surface area (ASTM D4567) between about 40 to about 60 square meters per gram (m$^2$/g). The catalysts particularly preferred have surface areas of about 49 to 53 m$^2$/g. The alumina catalyst should also be of a high purity, with a concentration of alumina in the catalyst greater than 80 weight percent, preferably greater than 90 weight percent, and more preferably greater than 95 weight percent, such as 99 weight percent alumina. The catalyst can be used in any of the conventional forms available commercially, such as, for example, in the extruded, tablet or powder form.

The hydrolysis reaction can be carried out in any reactor configuration which can promote intimate contact among the hydroformylation reaction product, steam or water, and the alumina catalyst. The reaction can be carried out batchwise, semi-batchwise or continuously. Preferably, the reaction is carried out continuously in a fixed bed reactor. Although the reaction can occur either in the liquid or gas phase, a liquid phase reaction is preferred. The most preferred reactor configuration is a "trickle" bed reactor in which an inert gas, such as nitrogen or hydrogen, is bubbled either cocurrently or countercurrently through a continuous liquid feed inside a fixed bed reactor to increase the contact efficiency between the feed and catalyst.

The amount of catalyst required to catalyze the hydrolysis reaction depends on the form of the catalyst, the reactor configuration and any limitations on required reaction time. The amount of catalyst required can be readily determined empirically. Advantageously, the amount of catalyst required is an amount such that the weight ratio of feed to catalyst is between about 4 to about 24 lbs feed/hr/lb catalyst. For a fixed bed reactor operating in the liquid phase, this translates into a liquid hourly space velocity between about 4 to about 20 hr$^{-1}$.

The temperature during hydrolysis is desirably at least 400° F. to achieve significant improvements in the conversion of acetal and formate impurities. Although the hydrolysis can be carried out at lower temperatures, the conversion of acetal and formate impurities decreases at such lower temperatures. The upper temperature limit depends primarily on desired energy usage and reactor equipment limitations. Preferably, the hydrolysis temperature is between about 400 to about 600° F., more preferably between about 400 to about 535° F., and more preferably between about 445 to about 505° F.

Advantageously, the concentration of water or steam present during hydrolysis is minimized to prevent the formation of separate water and hydrocarbon phases. The hydrolysis can be effectively carried out by having equimolar amounts of water or steam and acetal and formate impurities. Of course, such an amount of water or steam will depend on the composition of the hydroformylation reaction product. Preferably, if the reaction were conducted in the liquid phase, then the water to feed volume ratio is between about 4 to about 12.

The hydrolysis reaction pressure depends on equipment limitations, and in many instances will depend on the reactor pressure for the subsequent hydrogenation step. Most conventional oxo process equipment rarely if ever exceeds a pressure limitation of 4,000 psig. Another determining factor in setting the hydrolysis reaction pressure is the desirability to operate in the gas or liquid phase. For the preferred liquid phase operation, the pressure advantageously is between about 100 to about 4,000 psig, preferably between about 3,000 to about 3,500 psig. For gas phase operation, it is desirable as well as most convenient to operate at or near atmospheric pressure.

The improved process according to the present invention increases the yield of oxo alcohol by converting a substantial amount of acetal impurities in the demetalled hydroformylation reaction product to the corresponding aldehyde or alcohol during the catalytic hydrolysis step. Although the amount of acetal impurities converted will vary depending on the process conditions and reactor configuration, the amount of acetal impurities converted to aldehyde or alcohol will in preferred embodiments be no less than 70 mole percent, preferably no less than 80 mole percent, and more preferably no less than 90 mole percent. Following hydrolysis, the demetalled hydroformylation reaction product can be hydrogenated to further increase the overall yield of desired oxo alcohol.

The following examples illustrate and are not intended in any way to limit the scope of the claimed invention.

Improved acetal conversion by use of low surface area alumina is illustrated in this example.

A 316 stainless steel, ½" diameter reactor with appropriate high pressure connectors is charged with 35 cubic centimeters of alumina material to be tested. The catalyst loaded reactor is immersed in a fluid-bed sand bath equipped with electrical heaters for temperature control. Appropriate mechanical connections are installed to allow reactor operation at nominal pressure of 3,000 psig and nominal temperature of 475°. Under steady state conditions liquid feed and gaseous high purity (>99 vol % $H_2$) hydrogen are pumped over the fixed catalyst bed. Liquid product is depressured and sampled periodically. Aliquots of liquid product and liquid feed are analyzed for composition by gas chromatography.

The liquid feed consists of demetalled hydroformylation product of crude branched decanal, mixed with water at nominal water/feed of 4 vol %. Typical crude decanal component distribution appears in Table 1, below.

TABLE 1

| Crude decanal feed composition | | | | |
|---|---|---|---|---|
| Feed Name | Lights, Wt % (Paraffins & Olefins) | Aldehyde + Alcohol + Formate, Wt % | Heavy, Wt % (Dimeric & Higher Ethers; Ethers & Ether Alcohol | Acetal, Wt % |
| AA | 13.31 | 52.93 | 8.09 | 25.68 |
| BB | 12.48 | 54.81 | 8.39 | 24.32 |
| CC | 16.24 | 51.37 | 7.24 | 25.15 |
| DD | 15.69 | 52.72 | 9.28 | 22.31 |
| EE | 13.81 | 47.43 | 8.73 | 30.03 |
| FF | 12.74 | 49.45 | 7.29 | 30.53 |
| GG | 12.98 | 48.88 | 7.29 | 30.85 |

Different high purity alumina materials of varying surface area values are presented in Table 2.

TABLE 2

| Alumina types and surface areas | |
|---|---|
| Alumina Type | BET Surface Area[1] $m^2/g$ |
| A | 49 |
| B | 53 |
| C | less than 1 |
| D | 237 |

[1]Surface area determined with nitrogen by single-point BET method (ASTM D4567)

Alumia types described in Table 2 were tested at conditions listed in Table 3. Product composition for different test samples included in Table 3 are determined by gas chromatography; calculated acetal conversion values are listed in column (13). Column (14) in Table 3 is calculated in reference to the corresponding feed acetal composition. Column (15) in Table 3 is calculated based on cumulative averages on data in the previous column. FIG. 1 is a graphical representation of column (15) in Table 3.

High acetal hydrolysis conversion is desired for increased alcohol yield, which is the desired end product of the hydroformylation process. Acetal conversion over the different types of alumina is used to rank catalytic hydrolysis effectiveness.

FIG. 1 presents acetal conversion in excess of 80% for alumina types A and B, which have corresponding surface area values of 49 $m^2/g$ and 53 $m^2/g$. High acetal hydrolysis conversion is maintained from the start of the experiment for alumina types A and B. Alumina types C (less than 1 $m^2/g$) and D (237 $m^2/g$) exhibit inferior acetal hydrolysis conversion over the initial 1,000 hrs of operation.

TABLE 3

| Summarized hydrolysis test conditions and results | | | | | | | | | |
|---|---|---|---|---|---|---|---|---|---|
| (1) ALUMINA TYPE | (2) FEED NAME | (3) ONSTREAM TIME, hrs | (4) TEMP F. | (5) PRESS psig | (6) H2 RATE SL/hr | (7) FEED RATE, cc/hr | (8) WATER to FEED, vol % | (9) SPACE TIME hr | (10) LIGHTS WT % |
| A | AA | 89 | 475 | 2992 | 108 | 130 | 3.92 | 0.27 | 12.75 |
| A | AA | 113 | 475 | 3007 | 108 | 133 | 3.83 | 0.26 | 12.71 |
| A | AA | 137 | 475 | 2958 | 109 | 132 | 3.86 | 0.27 | 12.66 |
| A | AA | 161 | 475 | 3019 | 106 | 130 | 3.92 | 0.27 | 12.50 |
| A | BB | 329 | 475 | 3016 | 107 | 132 | 3.86 | 0.27 | 12.30 |
| A | CC | 1005 | 475 | 2987 | 98 | 139 | 3.67 | 0.25 | 15.97 |
| A | DD | 1533 | 475 | 2984 | 104 | 137 | 3.72 | 0.26 | 15.42 |

TABLE 3-continued

Summarized hydrolysis test conditions and results

| | | | | | | | | | |
|---|---|---|---|---|---|---|---|---|---|
| B | AA | 113 | 475 | 3000 | 103 | 140 | 3.64 | 0.25 | 12.89 |
| B | AA | 137 | 475 | 3021 | 104 | 133 | 3.83 | 0.26 | 12.80 |
| B | AA | 161 | 475 | 2998 | 104 | 119 | 4.29 | 0.29 | 12.47 |
| B | BB | 329 | 475 | 2993 | 104 | 133 | 3.83 | 0.26 | 12.64 |
| B | CC | 1005 | 475 | 2989 | 95 | 141 | 3.55 | 0.25 | 15.28 |
| B | DD | 1533 | 475 | 2969 | 102 | 130 | 3.92 | 0.27 | 14.68 |
| C | EE | 88 | 475 | 3000 | 103 | 134 | 3.73 | 0.26 | 12.43 |
| C | EE | 160 | 475 | 3000 | 103 | 129 | 3.88 | 0.27 | 12.62 |
| C | EE | 282 | 475 | 3020 | 99 | 126 | 3.97 | 0.28 | 12.70 |
| C | EE | 497 | 475 | 3038 | 100 | 134 | 3.73 | 0.26 | 13.08 |
| C | FF | 947 | 473 | 3014 | 105 | 164 | 3.05 | 0.21 | 12.94 |
| C | FF | 1139 | 475 | 3007 | 100 | 129 | 3.88 | 0.27 | 12.74 |
| C | FF | 1235 | 475 | 3004 | 101 | 124 | 4.03 | 0.28 | 12.73 |
| C | GG | 1427 | 475 | 3013 | 101 | 130 | 3.85 | 0.27 | 12.64 |
| D | EE | 88 | 475 | 3000 | 112 | 129 | 3.88 | 0.27 | 13.94 |
| D | EE | 160 | 475 | 3000 | 117 | 131 | 3.82 | 0.27 | 12.74 |
| D | EE | 282 | 475 | 3020 | 115 | 132 | 3.79 | 0.27 | 13.09 |
| D | EE | 497 | 475 | 3004 | 113 | 131 | 3.82 | 0.27 | 12.82 |
| D | FF | 947 | 473 | 3008 | 117 | 132 | 3.79 | 0.27 | 12.60 |
| D | FF | 1139 | 475 | 3002 | 110 | 130 | 3.85 | 0.27 | 12.70 |
| D | FF | 1235 | 475 | 3000 | 131 | 112 | 3.82 | 0.27 | 12.44 |
| D | GG | 1427 | 475 | 2995 | 132 | 114 | 3.79 | 0.27 | 12.74 |

| (1) ALUMINA TYPE | (2) FEED NAME | (11) ALDEHYDE ALCOHOL FORMATE WT % | (12) HEAVY WT % | (13) ACETAL WT % | (14) PERCENT ACETAL CONVERSION | (15) CUMULATIVE AVERAGE PERCENT ACETAL CONVERSION |
|---|---|---|---|---|---|---|
| A | AA | 73.30 | 9.96 | 4.00 | 84.42 | 84.42 |
| A | AA | 73.87 | 9.51 | 3.91 | 84.77 | 84.60 |
| A | AA | 73.75 | 9.70 | 3.89 | 84.85 | 84.68 |
| A | AA | 73.96 | 9.89 | 3.66 | 85.75 | 84.95 |
| A | BB | 75.37 | 9.34 | 2.99 | 87.71 | 85.50 |
| A | CC | 72.07 | 8.93 | 3.03 | 87.95 | 85.91 |
| A | DD | 71.56 | 10.01 | 3.01 | 86.51 | 85.99 |
| B | AA | 73.61 | 9.06 | 4.44 | 82.71 | 82.71 |
| B | AA | 73.21 | 9.41 | 4.59 | 82.13 | 82.42 |
| B | AA | 73.96 | 9.32 | 4.26 | 83.41 | 82.75 |
| B | BB | 74.49 | 8.74 | 4.13 | 83.02 | 82.82 |
| B | CC | 70.60 | 8.60 | 5.52 | 78.05 | 81.86 |
| B | DD | 70.96 | 9.36 | 4.99 | 77.63 | 81.16 |
| C | EE | 71.89 | 7.95 | 7.68 | 74.43 | 74.43 |
| C | EE | 70.74 | 8.13 | 8.51 | 71.66 | 73.04 |
| C | EE | 72.64 | 8.03 | 6.64 | 77.89 | 74.66 |
| C | EE | 74.49 | 7.85 | 4.58 | 84.75 | 77.18 |
| C | FF | 75.74 | 7.62 | 3.71 | 87.85 | 79.31 |
| C | FF | 76.03 | 7.68 | 3.55 | 88.37 | 80.82 |
| C | FF | 76.32 | 7.66 | 3.30 | 89.19 | 82.02 |
| C | GG | 76.73 | 7.48 | 3.16 | 89.76 | 82.99 |
| D | EE | 63.51 | 10.74 | 11.82 | 60.64 | 60.64 |
| D | EE | 66.45 | 9.87 | 10.95 | 63.54 | 62.09 |
| D | EE | 70.11 | 9.24 | 7.56 | 74.83 | 66.33 |
| D | EE | 71.11 | 9.14 | 6.94 | 76.89 | 68.97 |
| D | FF | 73.79 | 8.78 | 4.83 | 84.18 | 72.01 |
| D | FF | 74.45 | 8.46 | 4.39 | 85.62 | 74.28 |
| D | FF | 74.61 | 8.61 | 4.34 | 85.78 | 75.92 |
| D | GG | 74.22 | 8.82 | 4.22 | 86.32 | 77.22 |

We claim:

1. In the process for increasing the yield of an oxo alcohol prepared from the hydrogenation of a demetalled hydroformylation reaction product by hydrolyzing prior to hydrogenation the reaction product at conditions sufficient to convert an amount of acetal impurities in the reaction product to the corresponding aldehyde or alcohol, the improvement comprising the step of conducting the hydrolysis in the presence of a catalytically effective amount of an alumina catalyst having a surface area between about 40 to about 60 $m^2/g$ and at a hydrolysis temperature between about 400 to about 600° F. and at a hydrolysis pressure between about 3,000 to about 3,500 psig.

2. The process of claim 1 wherein the hydroformylation reaction product is the reaction product of a branched $C_{5-12}$ monoolefin with carbon monoxide and hydrogen.

3. The process of claim 2 wherein the alumina catalyst has a surface area between about 49 to about 53 $m^2/g$.

4. The process of claim 1, 2 or 3 wherein the hydrolysis is conducted continuously in a fixed bed reactor in the liquid phase.

5. The process of claim 4 wherein the amount of alumina catalyst is an amount such that the liquid hourly space velocity is between about 4 to about 20 $hr^{-1}$.

6. The process of claim 1 wherein the hydrolysis temperature is between about 400 to about 535° F.

7. The process of claim 1 wherein the hydrolysis temperature is between about 445 to about 505° F.

8. The process of claim 1 wherein the volume ratio of water to demetalled hydroformylation reaction product is between about 4 to about 12.

9. The process of claim 1 wherein the amount of acetal impurities converted to the corresponding aldehyde or alcohol is no less than 80 mole percent.

* * * * *